US010052171B1

(12) United States Patent
Almalki (10) Patent No.: US 10,052,171 B1
(45) Date of Patent: Aug. 21, 2018

(54) INTRAORAL MULTIFUNCTIONAL DENTAL TOOL

(71) Applicant: Naif A. Almalki, Norman, OK (US)

(72) Inventor: Naif A. Almalki, Norman, OK (US)

( * ) Notice: Subject to any disclaimer, the term of this patent is extended or adjusted under 35 U.S.C. 154(b) by 0 days.

(21) Appl. No.: 15/482,216

(22) Filed: Apr. 7, 2017

(51) Int. Cl.
*A61C 1/00* (2006.01)
*A61B 1/247* (2006.01)
*A61B 1/00* (2006.01)
*A61B 1/045* (2006.01)
*A61B 1/05* (2006.01)
*A61B 13/00* (2006.01)
*A61C 5/90* (2017.01)
*A61C 17/02* (2006.01)
*A61C 17/06* (2006.01)

(52) U.S. Cl.
CPC ........ *A61C 1/0015* (2013.01); *A61B 1/00006* (2013.01); *A61B 1/00009* (2013.01); *A61B 1/00045* (2013.01); *A61B 1/00087* (2013.01); *A61B 1/00091* (2013.01); *A61B 1/00094* (2013.01); *A61B 1/00096* (2013.01); *A61B 1/00101* (2013.01); *A61B 1/045* (2013.01); *A61B 1/051* (2013.01); *A61B 1/247* (2013.01); *A61B 13/00* (2013.01); *A61C 5/90* (2017.02); *A61C 17/0208* (2013.01); *A61C 17/043* (2013.01)

(58) Field of Classification Search
CPC ..... A61C 1/0015; A61C 5/90; A61C 17/0208; A61C 17/043; A61B 1/00006; A61B 1/00009; A61B 1/00045; A61B 1/00087; A61B 1/00091; A61B 1/00094
See application file for complete search history.

(56) References Cited

U.S. PATENT DOCUMENTS

| 1,122,086 A | * | 12/1914 | Dunlop | A61C 1/088 433/29 |
| 4,589,846 A | * | 5/1986 | Annoni | A61B 1/06 433/30 |
| 4,611,992 A | * | 9/1986 | Lokken | A61C 17/0202 433/116 |
| 4,727,416 A | * | 2/1988 | Cooper | A61B 1/00091 348/164 |

(Continued)

FOREIGN PATENT DOCUMENTS

WO    WO 94/09718    5/1994

*Primary Examiner* — Nicholas Lucchesi
(74) *Attorney, Agent, or Firm* — Oblon, McClelland, Maier & Neustadt, L.L.P.

(57) ABSTRACT

A dental tool system a shell made of silicone having a hollow interior and an opening to allow placement of the dental tool around a tooth, a tool base disposed along the hollow interior of the shell, an interchangeable tool head supported by the tool base to hold a dental instrument to operate on the tooth, a flexible mirror disposed along the circumference of the hollow interior at a first angle from the interchangeable tool head to view progression of the dental instrument operating on the tooth, a spray supported by the tool base and positioned adjacent to the interchangeable tool head, a suction supported by the tool base and positioned adjacent to the opening of the hollow interior to allow suction of fluid around the tooth, one or more camera to capture an image of the tooth, and a controller configured to move the interchangeable tool head.

19 Claims, 9 Drawing Sheets (56) References Cited

U.S. PATENT DOCUMENTS

| | | | | |
|---|---|---|---|---|
| 4,917,603 A | * | 4/1990 | Haack | A61C 5/80 |
| | | | | 433/29 |
| 5,122,153 A | * | 6/1992 | Harrel | A61C 17/043 |
| | | | | 433/114 |
| 5,152,686 A | * | 10/1992 | Duggan | A61C 17/043 |
| | | | | 433/140 |
| 5,516,286 A | * | 5/1996 | Kushner | A61C 17/0211 |
| | | | | 433/136 |
| 5,931,669 A | | 8/1999 | Fornoff et al. | |
| 6,152,733 A | * | 11/2000 | Hegemann | A61C 17/22 |
| | | | | 433/216 |
| 6,201,880 B1 | * | 3/2001 | Elbaum | A61B 1/24 |
| | | | | 348/66 |
| 6,714,657 B1 | * | 3/2004 | Jacobs | A61B 1/247 |
| | | | | 382/100 |
| 2005/0084816 A1 | | 4/2005 | Mehdizadeh | |
| 2006/0115789 A1 | * | 6/2006 | Wishart | A61C 5/80 |
| | | | | 433/136 |
| 2016/0262856 A1 | * | 9/2016 | Atiya | A61C 9/0006 |

* cited by examiner

INTRAORAL MULTIFUNCTIONAL DENTAL TOOL

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

BACKGROUND

In dentistry, a typically dental operation such as filling or root canal involves use of multiple dental instruments. Two or more dental instruments like a drill, a scraper, a water spray, and a suction may be used simultaneously during the dental operation. Oftentimes, an assistant is required to operate multiple tools such as the drill, the water spray, and the suction simultaneously.

During the dental operation, a dental patient has to keep his/her mouth open which can be painful and tiring for the dental patient. As, the patient becomes tired, he/she may start closing the jaw, which can be problematic and interfere with the dental operation. As such, the assistant may be required to keep the mouth open.

There remains a continuing need to provide improved dental tools that can perform several functions so that the dental operation can be performed effectively and fast. Additionally, a cost-effective tool is highly desirable as the cost of having an assistant can be high.

SUMMARY

According to an embodiment of the present disclosure, there is provided a dental tool. The dental tool includes a shell made of silicone having a hollow interior and an opening to allow placement of the dental tool around a tooth, a tool base disposed along the hollow interior of the shell, an interchangeable tool head supported by the tool base to hold a dental instrument to operate on the tooth, a flexible mirror disposed along the circumference of the hollow interior at a first angle from the interchangeable tool head to view progression of the dental instrument operating on the tooth, a spray supported by the tool base and positioned adjacent to the interchangeable tool head, a suction positioned adjacent to the opening of the hollow interior to allow suction of fluid around the tooth, one or more camera to capture an image of the tooth; and a controller. The controller configured to capture a first image of the tooth via the one or more camera and display the first image, analyze and identify dental issues based on the captured first image, select and display a set of dental instruments based on the identified dental issues, determine whether a dental instrument is attached to the interchangeable tool head based on a second image captured by one or more camera, send a message to attach the dental instrument to the interchangeable tool head, receive an input command to move the dental instrument to a desired position to perform a dental operation, send signal to activate the dental instrument, the spray and the suction, determine whether a dental operation is complete based on a third image capture, and retract the dental instrument upon completion of the dental operation.

Further, according to an embodiment of the present disclosure, there is provided a method for controlling a dental tool. The method includes capturing, via one or more camera, a first image of the tooth captured and displaying, via processing circuitry, the first image; analyzing, via the processing circuitry, and identifying, via the processing circuitry, dental issues based on the captured first image, selecting, via the processing circuitry, and displaying, via the processing circuitry, a set of dental instruments based on the identified dental issues, determining, via the processing circuitry, whether a dental instrument is attached to an interchangeable tool head based on a second image captured by the one or more camera, sending, via the processing circuitry, a message to attach the dental instrument to the interchangeable tool head, receiving, via the processing circuitry, an input command to move the dental instrument to a desired position to perform a dental operation, sending, via the processing circuitry signal to activate the dental instrument, a spray and a suction, determining, via the processing circuitry, whether the operation is complete based on a third image capture; and retracting, via the processing circuitry, the dental instrument.

Further, according to an embodiment of the present disclosure, there is provided a non-transitory computer-readable medium which stores a program which, when executed by a computer, causes the computer to perform the method for controlling a dental tool, as discussed above.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) may be practiced without those specific details. In some instances, well-known structures and components may be shown in block diagram form in order to avoid obscuring the concepts of the disclosed subject matter.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "proximate," "minor," and similar terms generally refer to ranges that include the identified value within a margin of 20%, 10% or preferably 5% in certain embodiments, and any values therebetween.

Figure 1:
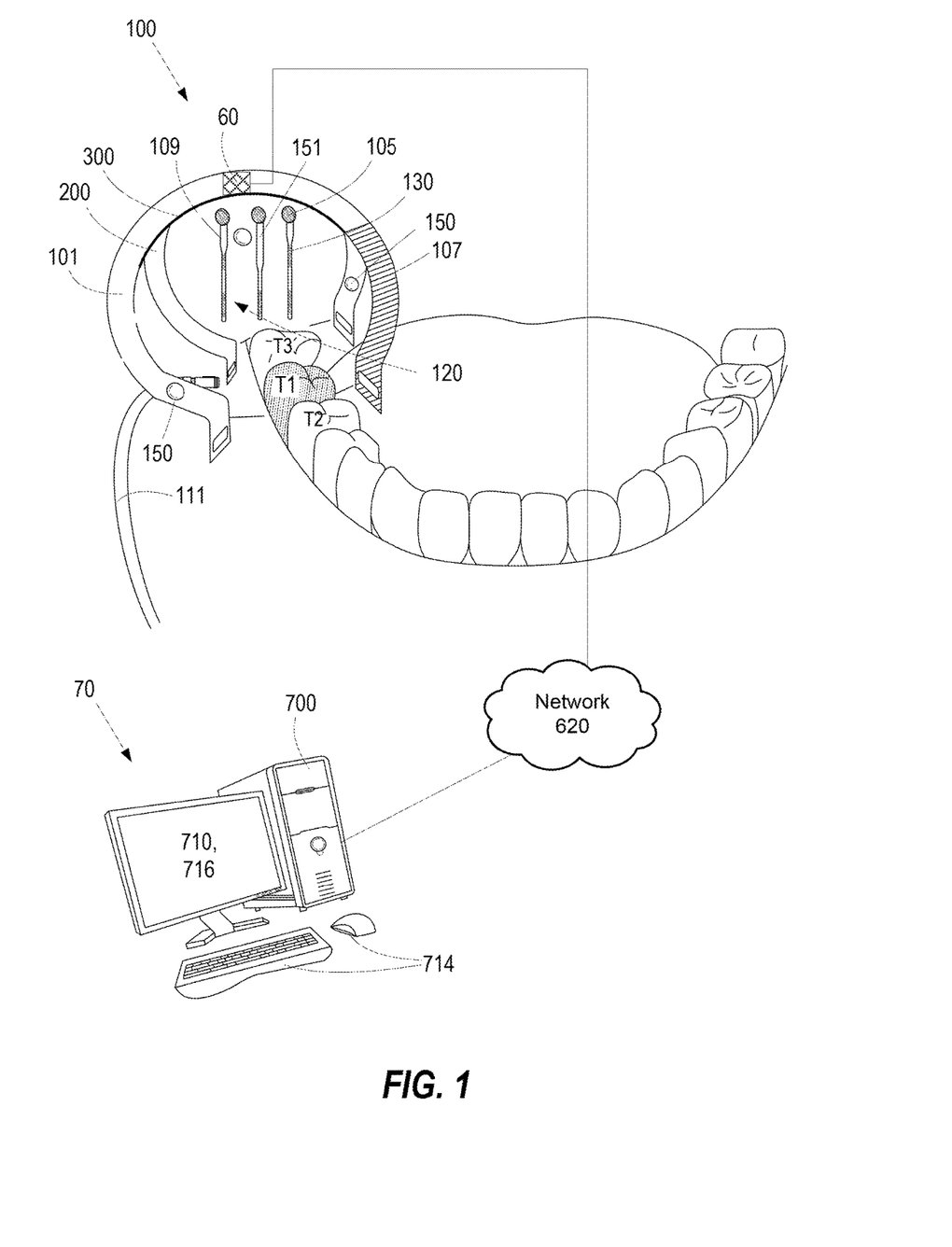
FIG. 1 illustrates a dental tool according to an exemplary embodiment of the present disclosure.

FIG. 1 illustrates a dental tool 100 according to an exemplary embodiment of the present disclosure. The dental tool 100 includes a shell 101, an interchangeable tool head 105, a flexible mirror 107, a spray 109, a suction 111, a tool base 300 and a controller 60. The dental tool 100 can also include one or more camera 150. The controller 60 can control a motion (or other relevant operation) of different components of the dental tool 100 such as the interchangeable tool head 105, the spray 109, and the suction 111. For example, the controller 60 can control the orientation and motion of the interchangeable tool head 105, a flow rate of water from the water spay 109, the ON/OFF of the suction 111, or a combination thereof.

In operation, the dental tool 100 can be placed over a tooth T1 or a set of teeth (e.g., teeth T1-T3) with an opening 120 facing towards an operator (e.g., a dentist or a nurse). As such, the operator has a visual access to an operation (e.g., drilling, cleaning, extracting, suction, etc.) being performed on the tooth T1. The operator can monitor the progress of the operation so that appropriate corrective measures (e.g., stop a drill, retract the drill or extractor, re-orient the drill or extractor, etc.) can be taken as necessary.

The camera 150 can be placed within the shell 101 in at approximately center of the shell close to the interchangeable tool head 105. The camera 150 can capture live video, and images of objects located the inside of the shell 101. The video and images can be stored in a memory of the controller 60 and used for diagnostic analysis or monitoring purposes. The live video can also guide the user to maneuver the interchangeable tool head 105 to desired location during a dental operation. Additional cameras 150 can also be on a spacer 200 and/or on a side within the shell 101 to capture multiple views of the dental operation within the shell 101.

The shell 101 has a hollow interior with the opening 120. The opening 120 allows placement of the dental tool 100 around a tooth as well as provides access to the hollow interior of the shell 101. The tool base 300, the interchangeable tool head 105, the flexible mirror 107, the spray 109, and the suction 111 can be disposed within the hollow interior of the shell 101 and each of the aforementioned components can be accessed via the opening 120 during operation of the dental 100.

Figure 2:
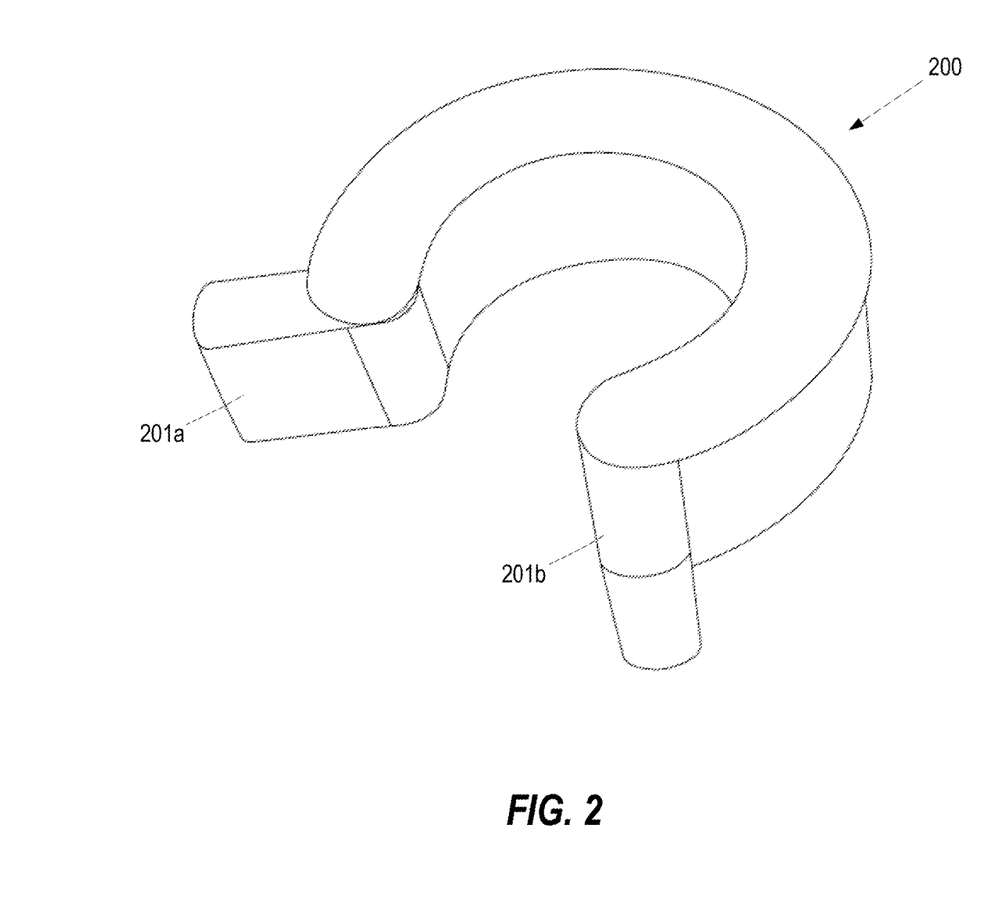
FIG. 2 illustrates a spacer of the dental tool according to an exemplary embodiment of the present disclosure.

The shell 101 can be made of silicone or other soft material that will not irritate or harm the interior of the mouth when the dental tool 100 is placed over the teeth T1-T3. Further, the shell 101 can be spherical in shape. The shell 101 can deform (expand or contract) depending on the opening or closing of the mouth. As such, when the shell 101 expands, the shell 101 can act as a cheek and tongue retractor. The expansion and contraction can also be controlled by including a ring-shaped spacer 200 disposed in the hollow interior of the shell 101. FIG. 2 illustrates an example spacer 200.

As shown in FIG. 2, the spacer 200 has a ring-like shape with a gripper 201a and 201b (also referred as gripper 201) extending towards the outside the ring. When placed within the dental tool 100 (in FIG. 1), the gripper 201 can be accessed via the opening 120 to expand (or contract) the shell 101. Thus, providing additional space around the tooth T1 during the operation.

Referring back to FIG. 1, the interchangeable tool head 105 can hold or grip a dental instrument 130 (also referred as a desired dental instrument) used to operate on a tooth. The interchangeable tool head 105 can be any joint or fixture that allows orientation of the attached dental instrument in a spherical space defined by the hollow interior of the shell 101. For example, the interchangeable tool head 105 can be a spherical joint 400, further illustrated in FIG. 4.

Alternatively, the interchangeable tool head 105 can be a movable piston with a spherical joint. The dental instrument 130 can be attached to the piston, which can be advanced (or retracted) to the tooth based on the user command received by the controller 60.

Figure 4:
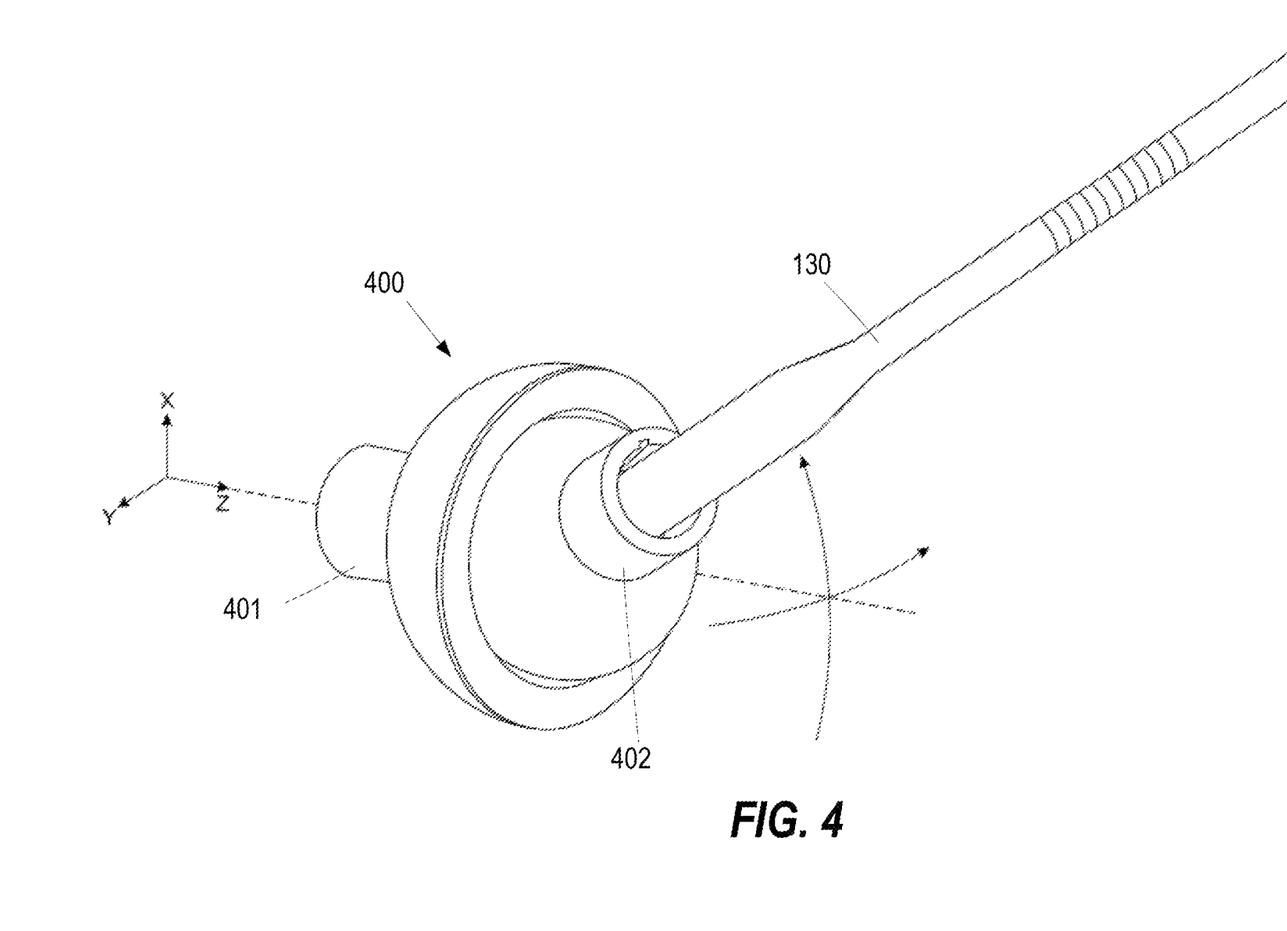
FIG. 4 illustrates a spherical joint of the dental tool according to an exemplary embodiment of the present disclosure.

FIG. 4 illustrates the spherical joint 400, which is an exemplary representation of the interchangeable tool 105. The spherical joint 400 can include a base 401 and an arm 402. The base 401 is a fixed part that can be attached to the tool base 300 (in FIG. 1). The arm 402 can rotate with respect to the base 401. The arm 402 also serves as fixture to attach a dental instrument 130 (e.g., a drill, a spray 109, an extractor, a suction 111, or other dental instruments). The dental instrument 130 can be removably attached to the arm 402 using different snap and release mechanism such as snap fitting, spring-activated locks, etc. The arm 402 allows a 360° rotation of the dental instrument 130. The rotation of the arm 402 can be controlled by the controller 60 based on the inputs received from the user (e.g., the dentist). The spherical joint 400 can be adapted to fit different types of dental instruments. The desired dental instrument can be pre-installed before placing the dental tool 100 around the tooth T1 (in FIG. 1).

Referring back to FIG. 1, the flexible mirror 107 can be a single mirror with flexible reflective surface or a group of mirrors arranged in an array like structure within the wire frame of the tool base 300. The flexible mirror 107 can be disposed along the circumference of the hollow interior at a first angle θ (in FIG. 2) from the interchangeable tool head 105 to view progression of the dental instrument 130 operating on the tooth.

The spray 109 is a device that can spray water or other fluid over a tooth on demand. The spray 109 can be supported by the tool base 300 and positioned adjacent to the interchangeable tool head 105. The spray 109 is positioned such that it does not interfere with the operation of the interchangeable tool head 105 or the dental instrument 130 attached to the interchangeable tool head 105.

The suction 111 can be a pipe connected to a pump (not illustrated) that allows suction of fluid (e.g., water, saliva, blood, etc.) accumulated within the dental tool 100. The suction 111 can be supported by the tool base 300 and positioned adjacent to the opening 120 of the hollow interior to allow suction of fluid around the tooth being operated.

The controller 60 can be a processing circuitry or electronics circuit implementing functions to control the operation of the dental tool 100. The controller 60 can be configured to, for example, receive motion signal to move the interchangeable tool head 105 to a desired location, activate the spray 109, activate the suction 111, capture an image using the camera 150, and retract the interchangeable tool head 105.

The dental tool 100 can further include a helper tool head 151 attachment to removably attach a helper tool (e.g., a mirror, an explorer tool, a scaler, a tweezer, a carver, a curette, etc.) that operates in coordination with the dental instrument 130 (e.g., a drill or extractor) attached to the interchangeable tool head 105. For example, for a dental filling operation, a carver can be used (along with a filling instrument attached to the interchangeable tool head 105) to press or shape the dental filling. The carver can be reciprocated back and forth or in a circular manner to densely pack the dental filling, shape the filling or remove excess material.

The dental tool 100 further includes the expandable spacer (or a ring) 200 that expands or contacts to maintain the desired location of the desired dental instrument while operating on the tooth. The spacer 200 can also be connected to the tool base 300 to maintain the form of the tool base 300.

The tool base 300 can be disposed along the hollow interior of the shell 101. The tool base 300 can support different components of the dental tool 100 or other dental instruments. For example, the tool base 300 provides support for the interchangeable tool head 105, the flexible mirror 107, the spray 109, and/or the suction 111. The structure of the tool base 300 is further illustrated and discussed later in the present disclosure with respect to FIGS. 3A-3C.

Figure 3A:
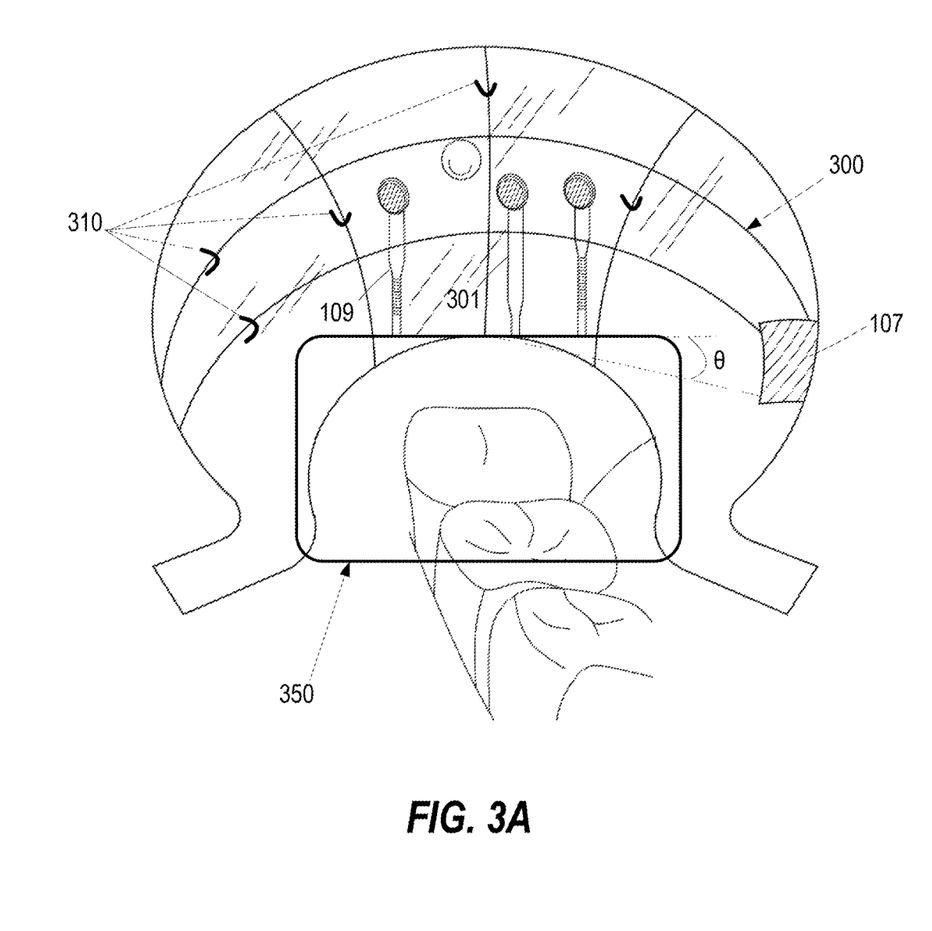
FIG. 3A illustrates a tool base of the dental tool according to an exemplary embodiment of the present disclosure.

FIG. 3A illustrates the tool base 300 according to an exemplary embodiment of the present disclosure. The tool base 300 disposed along the hollow interior of the shell 101. The tool base 300 can be a grid-like structure made from a wire frame. Alternatively or in addition, the tool base can be a surface including grooves (or channels) within which the tool head 105 can move. The wireframe can include one or more pinchable loop 310 to removably attach the tool base 300 to the shell 101. Pinchable loops can be snap fit type of attachments that can grab the skin of the shell 101 in a pinchable manner, for example, like a clip. As such, the tool base 300 can be removed to repair or replace a damaged interchangeable tool head, repair a wire frame, change and install a different configuration of a set of dental instruments like a drill 301, a spray 109, a extractor, a suction 111, or other dental instruments. For example, in one configuration, the dental tool 100 can include only the extractor located at the center of the tool base 300. The extractor can be fixed and pre-oriented in a desired position to extract a tooth. Alternatively, the extractor can be moved and oriented based on orientation commands received from the controller 60. A second exemplary configuration can include the drill 301 located at the center of the tool base 300 and the spray 109 located adjacent to the drill 301.

The dental tool further includes a transparent cover 350 disposed over the opening 120 in the shell 101 to prevent fluid from splashing outside the dental tool.

Figure 3B:
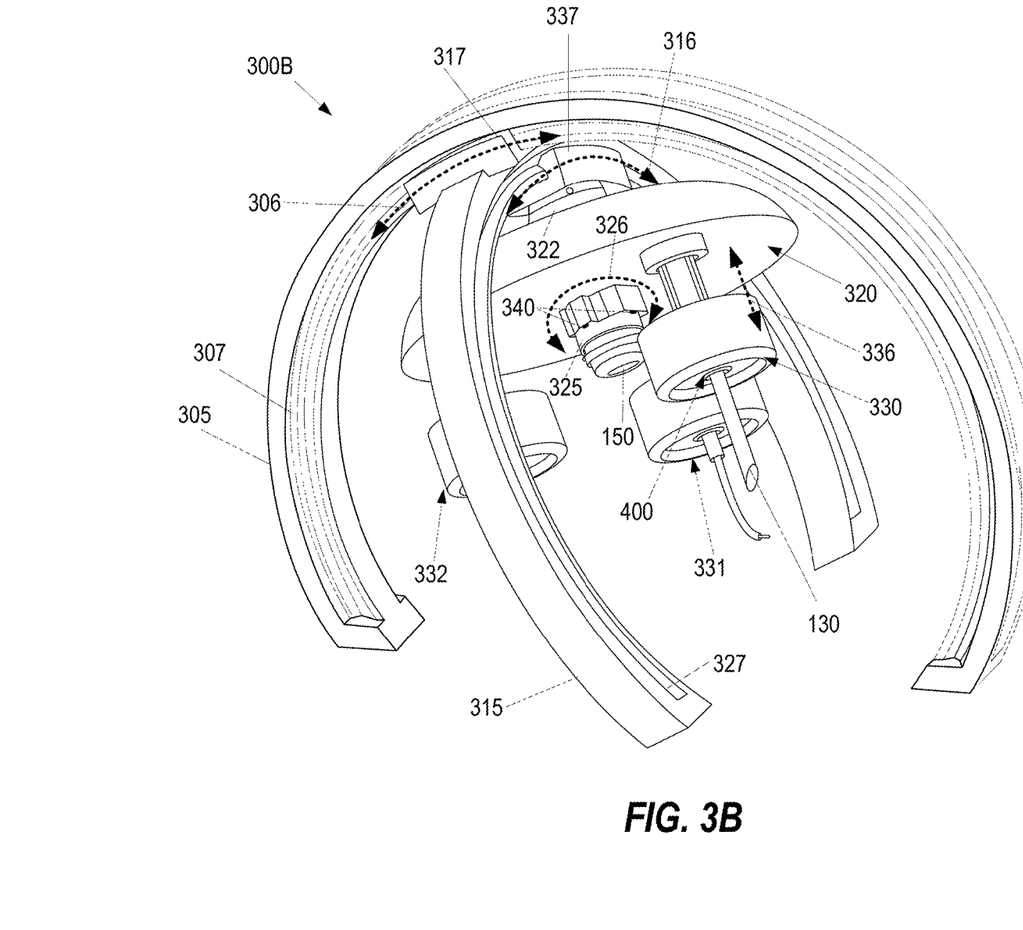
FIG. 3B illustrates a plate base with pistons according to an exemplary embodiment of the present disclosure.

In one embodiment, as illustrated in FIG. 3B, a tool base 300B can include a rotating plate or disc with attachments for dental instrument. The tool base 300B includes a first curved support 305 and a second curved support 315, and a disc 320. The first curved support 305 is movably connected to the second curved support 315. Furthermore, the first curved support 305 can be disposed in a in a significantly perpendicular manner with respect to the second curved support 315. As such, the second curved support 315 can move relative to the first curved support 305 in a first direction 306. The disc 320 is movably connected to the second curved support 315. The disc 320 can move relative to the second curved support 315 along a second direction 316 as well as rotate about a third direction 326.

The first curved support 305 is a rigid curved block of a size that can fit in an open mouth. The first curved support 305 includes a first channels 307 extending along the length of the first curved support 305. The first channels 307 support and guide the second curved support 315 moving in the first direction 306. The second curved support 315 is connected to the first channels 307 via a first slider 317. The first slider 317 can be a rectangular block adapted to slidably connect within the first channels 307 on one side, and rigidly fitted to the second curved support 315 on a second side. Alternatively, the first slider 317 can be wheels that fit within the first channels 307.

The second curved support 315 can also be a rigid curved block of a size that can be fitted in an open mouth. The second curved support 315 includes a second channels 327 extending along the length of the second curved support 315. The second channels 327 support and guide the disc 320 to move in the second direction 316. The plate 320 is connected to the second channels 327 via a second slider 337. The second slider 337 can be a rectangular block adapted to slidably connect within the second channels 327 on one side, and fitted to rotatably connect the disc 320 on a second side. Alternatively, the second slider 337 can be wheels that fit within the second channels 327.

The disc 320 can be a circular or an elliptical in shape having a shaft 322 and at least one hole to attach a piston 330 (and/or pistons 331 and 332) in a reciprocating manner. The disc 320 includes a motor 325 attached at a center of the disc 320 that allows the disc 320 to rotate about the shaft 322 in a circular manner in a third direction 326 relative to the second curved support 315. The piston 330 is configured to reciprocate in a fourth direction 336 relative to the disc 320. The piston 330 also includes the spherical joint 400 to which a dental instrument 130 can be attached.

Furthermore, the disc 320 can include lights 340 (e.g., LED lights) mounted around (or on) the motor 325 to light the interior of the shell 101 for better visibility. Also, the camera 150 can be mounted at the center of the motor 325 to capture a top view of the dental operation, teeth status, etc. Further, the camera 150 can be in communication with the lights 340 to capture a clear image or a video in case of low light situations. The lights 340 can be turned on or off via the controller 60 automatically or based on user input. Furthermore, the pistons 331 and/or the piston 332 can be attached with the dental instruments 130 (e.g., probe) that is similar or different from the dental instrument 130 (e.g., a drill) attached to the piston 300.

In operation, the controller 60 can control the movement of the second curved support 315 in the first direction 306 to orient the dental instrument 130 (e.g., the drill) in the first direction. Further, the controller 60 can control the movement of the disc 320 in the second direction 316 and/or the third direction 326 to orient the dental instrument like the drill 301 in the second direction 316 and/or the third direction 326. Once the dental instrument is positioned above the tooth (e.g., T1), the controller 60 can advance or retract the piston 330 in the fourth direction 336 to perform a dental operation with the dental instrument 130. A translation of the piston 330 can be performed via a motor that receives signal from the controller 60. For example, the piston 330 can be connected to a threaded shaft of the motor. As the motor receives a rotation signal from the controller 60, the piston can slide (up or down) along the threaded shaft, thus extending towards or retracting away from the teeth. Alternatively, a piston-cylinder arrangement that can be pneumatically activated can be used. The present disclosure is not limited to the sliding mechanism used to move the piston 330 and any mechanism as would be understood by one of ordinary skill in the art can be used.

Figure 3C:
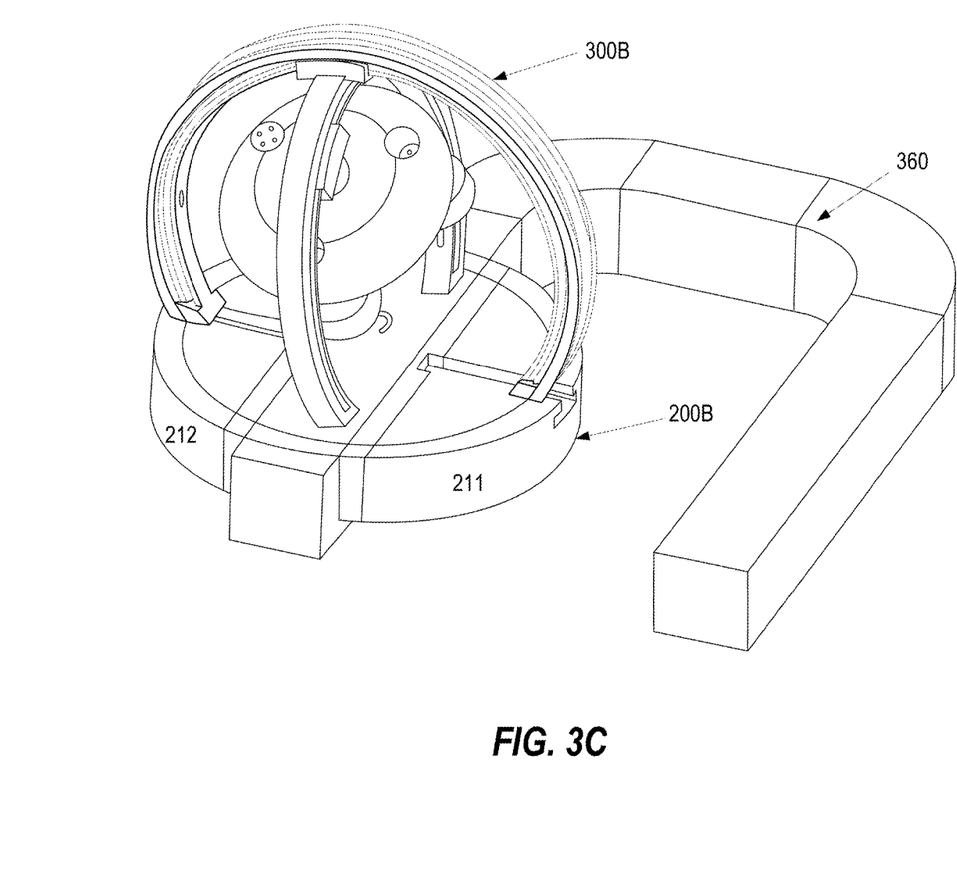
FIG. 3C illustrates a plate base with retractable supports of the dental tool according to an exemplary embodiment of the present disclosure.

FIG. 3C illustrates the dental tool 100 in operation. The dental tool 100 can include spacer 200B connected below the tool base 300B. The spacer 200B can be any device made of a first part 211 and a second part 212 having a semicircular shape. The first part 211 can be placed on a right side of the teeth within a jaw 360, and the second part 212 can be placed on a left side of the teeth within the jaw 360. The first part 211 and the second part 212 can be manually moved away from each other to retract a tongue or cheek to create space to operate on a tooth. The first part 211 can be manually slid away from the teeth to retract the tongue and/or the second part 212 can be manually slide away from the teeth to retract the cheek. The spacer 200B can also act as a support for the tool base 300B and prevent the tool base 300B from hurting the tongue, cheek or gums when a patient may bite on the dental tool 100.

Figure 5:
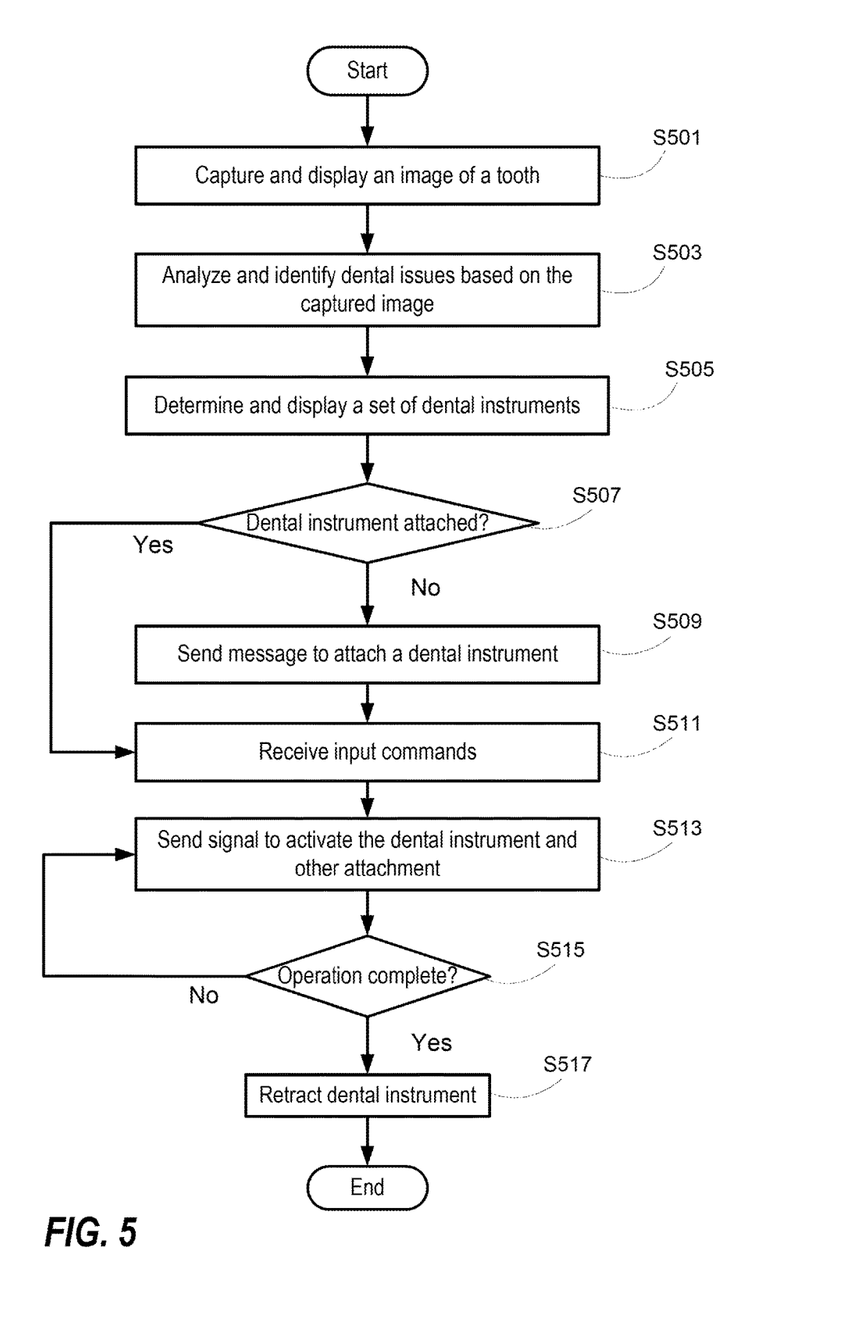
FIG. 5 is a flow chart for controlling the dental tool according to an exemplary embodiment of the present disclosure.

FIG. 5 is a flow chart for controlling the dental tool 100 according to an exemplary embodiment of the present disclosure. The controller 60 controls the operation of the dental tool 100. The controller 60 can start controlling the operation of the dental tool 100 when a user activates (or switches on) the controller 60.

In step S501, the computer 70 (and/or controller 60) can activate the camera 150 to capture an image (a first image), video of a tooth or an area within the shell 101 based on direct user activation or via the computer 70. Further, the controller 60 can send the image to a computer 70 to display the captured image (or video) on a display 710 to allow a user to monitor the tooth or dental operation. Based on the captured image, in step S503, the computer 70 (and/or controller 60) can be configured to analyze any dental issues such as cavities, decay, gum sores or blisters, tooth erosion, or other visibly detectable issues. The analysis of dental issue can be enabled using image processing software configured to detect and identify dental issues or anomalies.

In step S505, based on the identified dental issues (e.g., decay), the computer 70 (and/or controller 60) can determine a set of dental instruments (e.g., scraper, drill, spray, suction, etc.) that are commonly used to fix the identified dental issue. The computer 70 can display a list of identified (or desired) dental instruments on the display 710 to allow user to make appropriate tool selection. The user can select the dental instruments from the displayed list. Alternatively, the user can ignore the suggestion and choose other appropriate desired dental instrument based on user experience.

In step S507, the computer 70 (and/or controller 60) determines, based on the image (a second image) captured by one or more camera 150, whether a dental instrument (e.g., the identified dental instruments like scraper, spray and suction) is attached to the dental tool 100. If the dental instrument is not attached, in step 5509, the computer 70 (and/or controller 60) sends a signal to attach the dental instrument before proceeding with operating the dental tool 100. For example, computer 70 (and/or controller 60) can send a warning message to be displayed on the display 710.

When the identified dental instruments are attached, in step S511, the computer 70 can receive input commands from the user to operate the dental tool 100 and the computer 70 can further send the input commands to the controller 60. In step S513, the controller 60 can send signal to activate the dental instrument and other attachments. For example, the controller 60 can send signal to the interchangeable tool head 105 to move to a particular location (e.g., over the tooth T1 in FIG. 1) via the spherical joint 400 (in FIG. 4). For instance, the controller 60 can send signal to the arm 402 that holds the dental instrument 130 to rotate to a desired position. Further, the controller 60 can activate the dental instrument (e.g., scraper or a drill) attached to the interchangeable tool head 105.

The controller 60 can activate one or more dental instruments. For example, when cleaning a decayed tooth, the dental instrument selected can be a scrapper. Further, the spray can also be used to clean the decayed tooth and suction In step 5515, the computer 70 (and/or controller 60) determines whether the dental operation (e.g., scraping or drilling) performed by the user is complete. The determination can be based on the user input or by analyzing images (a third image) captured by the camera 150. For example, the first image captured before the dental operation can be compared with the third image captured after the dental operation is performed. The comparison can be based on measures such as depth of a cavity, spread (or area) of a decay, or other measurable factors. The user can indicate the operation is complete to via a mouse, keyboard or touch screen.

When the operation is complete, in step 5517, the computer 70 (and/or controller 60) sends signal to retract the dental instrument. Once, the instrument is retracted, the user can remove the dental tool 100 from a patients mouth to examine the operated tooth visually.

Figure 6:
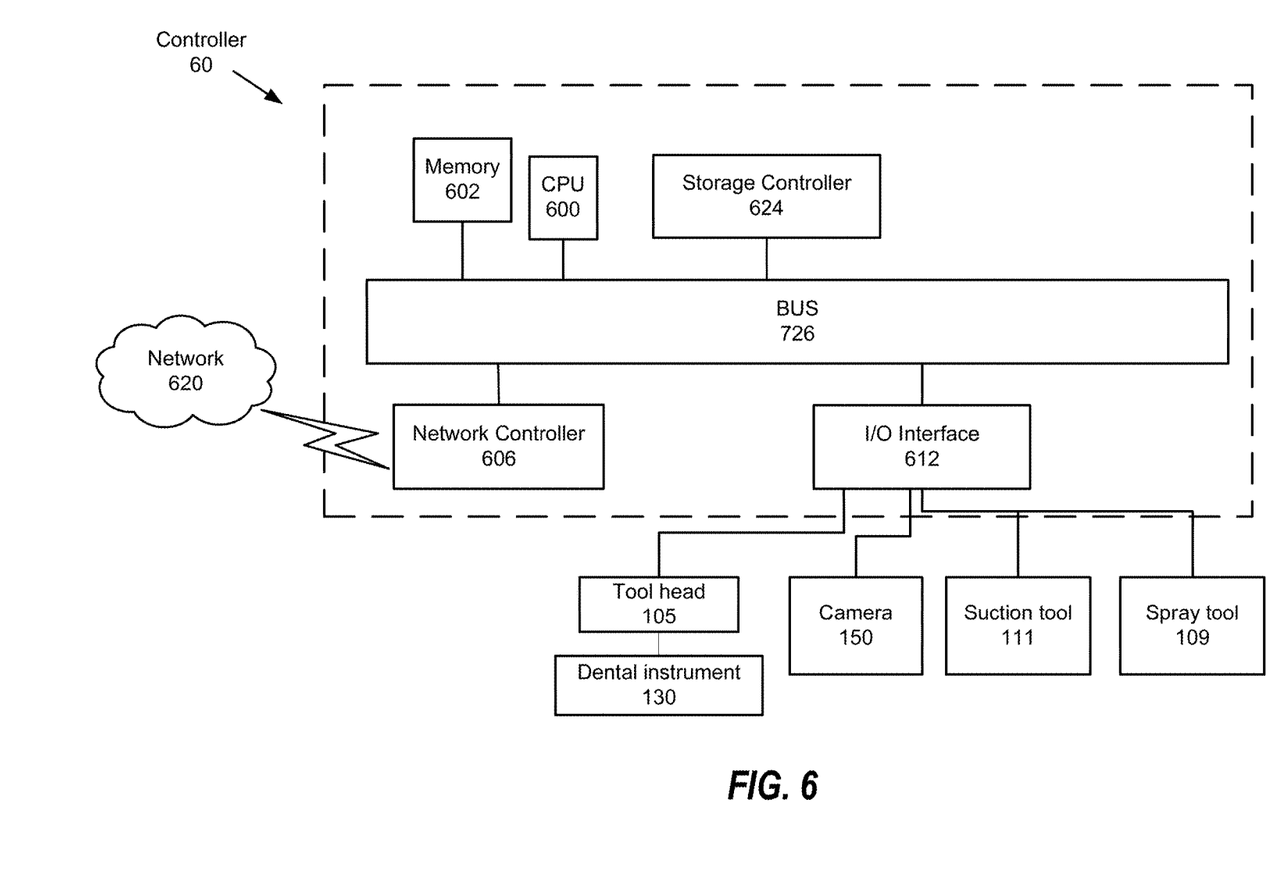
FIG. 6 is a block diagram illustrating a controller according to an exemplary embodiment of the present disclosure.

FIG. 6 is a block diagram illustrating the controller 60 according to an exemplary embodiment of the present disclosure. In FIG. 6, the controller 60 includes a CPU 600 which can be configured to receive inputs from the camera 150 and from a user via a keyboard/mouse 714 or a touch screen 716 of the computer 70, and process the data received from the camera 150 and the user to activate the tool head 105, the suction 111 and the spray 109. The CPU 600 can also be configured to analyze an image captured by the camera 150, determine a set of desired dental instruments and display the set of desired dental instruments for user selection. Furthermore, the CPU 600 can be configured to activate the dental instrument 130 such as a drill and a scraper attached to the tool head 105. The process data and instructions may be stored in the memory 602.

The hardware elements, in order to achieve the controller 60, may be realized by various circuitry elements, known to those skilled in the art. For example, CPU 600 may be a XENON or Core processor from INTEL of America or an Opteron processor from AMID of America, or may be other processor types that would be recognized by one of ordinary skill in the art. Alternatively, the CPU 600 may be implemented on an FPGA, ASIC, PLD or using discrete logic circuits, as one of ordinary skill in the art would recognize. Further, CPU 600 may be implemented as multiple processors cooperatively working in parallel to perform the instructions of the processes described above with respect to FIG. 5.

The controller 60, in FIG. 6, also includes a network controller 606 for interfacing with a network 620. Such network based interfacing can be useful to send commands, images or video captured by the camera 150, etc. to an external device such as a server (e.g., the computer 70) for analyzing the dental issues or monitoring the dental operation.

An I/O interface 612 interfaces the tool head 105, the camera 150, the suction 111 and the spray 109 to send and receive signals to the respective components.

The storage controller 624 connects the memory 602 with communication bus 626, which may be an ISA, EISA, VESA, PCI, or similar device, for interconnecting all of the components of the controller 60. A description of the general features and functionality of the storage controller 624, network controller 606, and the I/O interface 612 is omitted herein for brevity as these features are known.

Figure 7:
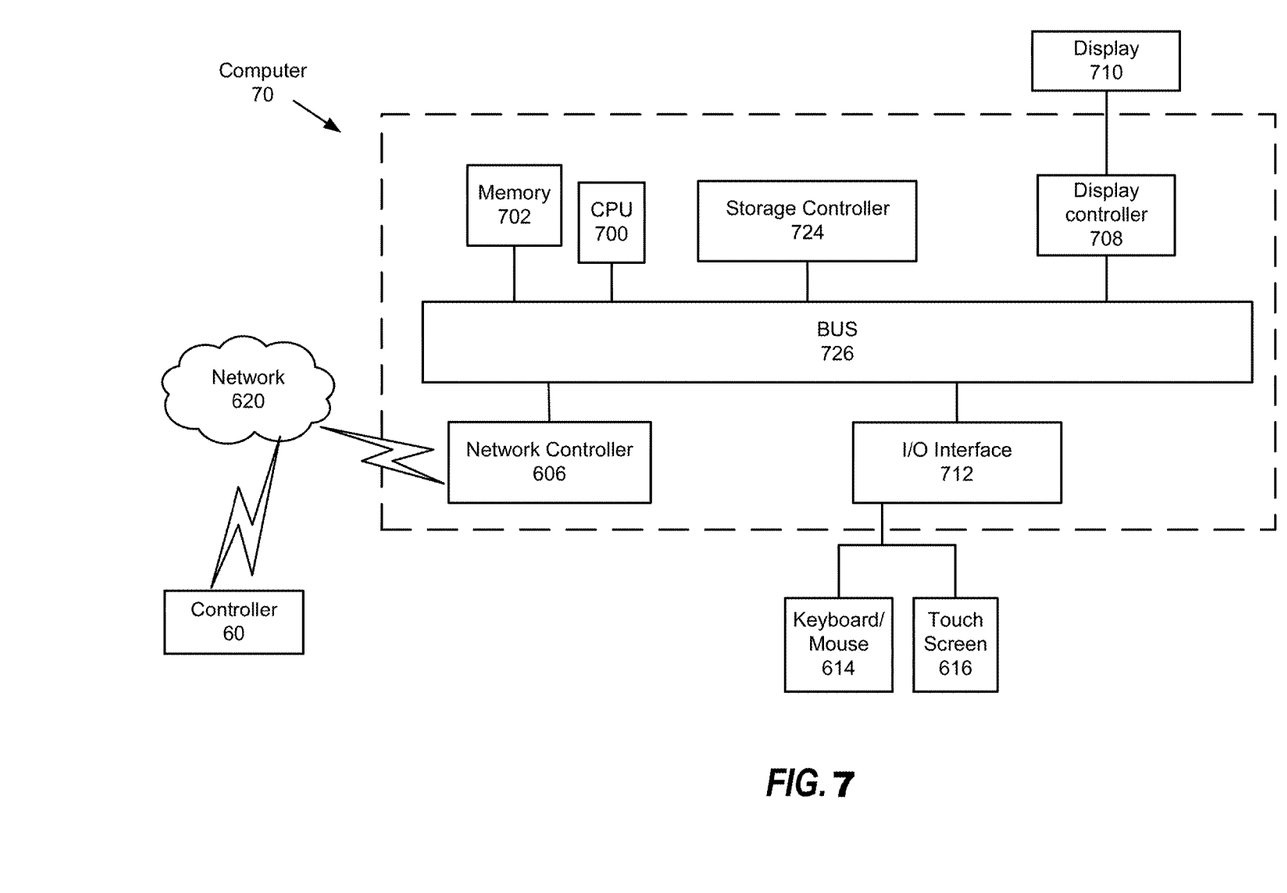
FIG. 7 is a block diagram illustrating a computer according to an exemplary embodiment of the present disclosure.

FIG. 7 is a block diagram illustrating the computer 70 according to an exemplary embodiment of the present disclosure. In FIG. 7, the computer 70 includes a CPU 700 which can be configured to receive inputs from the controller 60 and from a user via a keyboard/mouse 714 or a touch screen 716, and process the data received from the camera 150 and the user. Based on the processed data, the computer 70 can send signal to the controller 60. The CPU 700 can also be configured to analyze an image captured by the camera 150, determine a set of desired dental instruments and display the set of desired dental instruments for user selection. The process data and instructions may be stored in the memory 602.

The hardware elements, in order to achieve the computer 70, may be realized by various circuitry elements, known to those skilled in the art. For example, CPU 700 may be a XENON or Core processor from INTEL of America or an Opteron processor from AMD of America, or may be other processor types that would be recognized by one of ordinary skill in the art.

The computer 70, in FIG. 7, also includes a network computer 606 for interfacing with a network 620. Such network based interfacing can be useful to send or receive commands, images or video captured by the camera 150, etc. to an external device such as the controller 60 for analyzing the dental issues or monitoring the dental operation.

An I/O interface 612 interfaces the keyboard/mouse 714, touch screen 716, the tool head 105, the camera 150, the suction 111 and the spray 109 to send and receive signals to the respective components.

The computer 70 can further includes a display controller 608, such as a NVIDIA GeForce GTX or Quadro graphics adaptor from NVIDIA Corporation of America for interfacing with display 710, such as a Hewlett Packard HPL2445w LCD monitor. The display can be used to display information related to the image captured by the camera 150 and a suggestion of desired dental instruments or other appropriate messages related to a dental operation. In case of a touch screen activated display inputs like start and stop can be displayed as well. A general purpose I/O interface 712 interfaces with a keyboard and/or mouse 714 as well as a touch screen panel 716 on or separate from display 710.

The storage controller 724 connects the memory 702 with communication bus 726, which may be an ISA, EISA, VESA, PCI, or similar device, for interconnecting all of the components of the computer 70. A description of the general features and functionality of the storage controller 724, network controller 606, and the I/O interface 712 is omitted herein for brevity as these features are known.

While certain embodiments have been described, these embodiments have been presented by way of example only, and are not intended to limit the scope of the present disclosure. Indeed, the novel apparatuses and systems described herein can be embodied in a variety of other forms; furthermore, various omissions, substitutions and changes in the form of the apparatuses and systems described herein can be made without departing from the spirit of the present disclosures. The accompanying claims and their equivalents are intended to cover such forms or modifications as would fall within the scope and spirit of the present disclosure.

What is claimed is:

1. A dental tool system comprising:
   a dental tool having
      a shell having a hollow interior and an opening configured to be placed around a tooth;
      a tool base affixed along the hollow interior of the shell,
      an interchangeable tool head supported by the tool base and configured to hold a dental instrument to operate on the tooth,
      a flexible minor disposed along the circumference of the hollow interior at a first angle from the interchangeable tool head and configured to provide a view of the dental instrument operating on the tooth,
      a spray tool supported by the tool base positioned adjacent to the interchangeable tool head,
      a suction tool positioned adjacent to the opening of the hollow interior and configured to provide suction of fluid around the tooth,
      one or more cameras affixed along the hollow interior of the shell and configured to capture an image of the tooth, and
      a processor configured to control the spray tool, the suction tool and the one or more cameras: and
   a computer having a controller connected to the processor of the dental tool and configured to
      capture a first image of the tooth via the one or more cameras and display the first image,
      analyze and identify dental issues based on the captured first image,
      determine and display a set of desired dental instruments based on the identified dental issues,
      send a signal to the dental tool to activate a desired dental instrument of the displayed dental instruments, the spray tool and the suction tool, determine whether a dental operation is complete based on analysis of a third image captured via the one or more camera, and send a signal to the dental tool to retract the desired dental instrument upon completion of the dental operation.

2. The system according to claim 1, wherein the shell has a spherical shape acting as a cheek and tongue retractor.

3. The system according to claim 1, wherein the tool base has a grid-like structure made from a wire frame.

4. The system according to claim 1, wherein the interchangeable tool head has a spherical joint configured to provide rotation of the attached dental instrument in a spherical space.

5. The system according to claim 1, wherein the shell is made of silicone.

6. The system according to claim 1, the controller is further configured to determine whether the desired dental instrument is attached to the interchangeable tool head based on a second image captured via the one or more cameras, send a message to attach the desired dental instrument to the interchangeable tool head, and receive an input command from the compute o move the desired dental instrument to a desired position to perform a dental operation.

7. The system according to claim 1, further comprising:
a helper tool attachment to removably attach a helper tool configured to operate in coordination with the desired dental instrument.

8. The system according to claim 1, further comprising:
an expandable spacer attached to the tool base that expands or contacts the shell to maintain a desired position of the desired dental instrument.

9. The system according to claim 1, further comprising:
a transparent cover disposed over the opening in the shell to prevent fluid from splashing outside the dental tool.

10. The system according to claim 1, wherein the tool base includes a first curved support with a first channel defining a first direction of motion, a first slider slidably connected within the first channel of the first curved support, a second curved support with a second channel defining a second direction of motion, the second curved support movably connected to the first curved support via the first slider to allow the second curved support to move along the first direction, a second slider slidably connected within the second channel of the second curved support, and a disc movably connected to the second curved support via the second slider allowing the disc to move along the second direction and rotatably connected to a center of the disc allowing the disc to rotate in a third direction.

11. The system according to claim 10, wherein the disc further includes at least one piston that reciprocates relative to the disc in a fourth direction.

12. The system according to claim 11, the at least one piston includes a spherical joint to hold and orient the desired dental instrument.

13. The system according to claim 12, wherein the controller is further configured to move the second curved support in the first direction based on a received input command from the computer, move the disc in the second direction and rotate the disc in the third direction based on the received input command, and move the piston along the fourth direction based on the received input command.

14. The system according to claim 1, wherein the shell is made of silicone.

15. A dental tool comprising:
a shell having a hollow interior and an opening configured to be placed around a tooth;
a tool base affixed along the hollow interior of the shell;
an interchangeable tool head supported by the tool base and configured to hold a dental instrument to operate on the tooth;
a flexible mirror disposed along the circumference of the hollow interior at a first angle from the interchangeable tool head and configured to provide a view of the dental instrument operating on the tooth;
a spray tool supported by the tool base positioned adjacent to the interchangeable tool head:
a suction tool positioned adjacent to the opening of the hollow interior and configured to provide suction of fluid around the tooth,
one or more cameras affixed along the hollow interior of the shell and configured to capture an image of the tooth; and
a processor configured to control the spray tool, the suction tool and the one or more cameras.

16. The system according to claim 15, wherein the shell has a spherical shape acting as a cheek and tongue retractor.

17. The system according to claim 16, wherein the shell is made of silicone.

18. The system according to claim 15, wherein the tool base has a grid-like structure made from a wire frame.

19. The system according to claim 15, wherein the interchangeable tool head has a spherical joint configured to provide rotation of the attached dental instrument in a spherical space.

* * * * *